United States Patent [19]

Miike et al.

[11] Patent Number: 5,302,513
[45] Date of Patent: Apr. 12, 1994

[54] METHOD FOR DETERMINATION OF COMPONENTS

[75] Inventors: Akira Miike, Shizuoka; Toshio Tatano, Numazu, both of Japan

[73] Assignee: Kyowa Medex Co., Ltd., Tokyo, Japan

[21] Appl. No.: 727,369

[22] Filed: Jul. 9, 1991

Related U.S. Application Data

[63] Continuation of Ser. No. 465,121, Feb. 22, 1990, abandoned.

[30] Foreign Application Priority Data

Jun. 29, 1988 [JP] Japan .................................. 63-161148

[51] Int. Cl.$^5$ ........................ C12Q 1/48; C12Q 1/26; C12Q 1/37; C12Q 1/52
[52] U.S. Cl. ........................................ 435/15; 435/25; 435/26; 435/23; 435/16; 435/14; 435/4
[58] Field of Search .................. 435/25, 15, 26, 16, 435/14, 23, 4

[56] References Cited

U.S. PATENT DOCUMENTS 3,627,645  7/1969  Grassetti ............................ 435/25

OTHER PUBLICATIONS

Zubay, "Biochemistry"; pp. 878-882, 1983.
Hagen et al., Can J. Biochem. and Physiology, vol. 40, pp. 1129-1139 (1962).

Primary Examiner—Michael G. Wityshyn
Assistant Examiner—Louise N. Leary
Attorney, Agent, or Firm—Fitzpatrick, Cella, Harper & Scinto

[57] ABSTRACT

The present invention relates to a method for quantitative determination of NAD(P)H derived from a specific component, which comprises converting NAD(P)H present in a sample or formed from components other than the objective component by reactions into NAD(P) by the action of glutathione of oxidation type and glutathione reductase; decomposing the remaining glutathione of oxidation type by the action of γ-glutamyl transpeptidase in the presence or in the absence of a mercapto compound; forming NAD(P)H from the component to be determined in the sample utilizing an NAD(P)H-forming reaction system; and quantitatively determining NAD(P)H.

According to the method of the present invention, amylase activity, etc. in vital components containing maltose and glucose can be determined accurately.

10 Claims, 1 Drawing Sheet

METHOD FOR DETERMINATION OF COMPONENTS

This application is a continuation of application Ser. No. 07/465,121 filed Feb. 22, 1990, now abandoned.

INDUSTRIALLY APPLICABLE FIELD

The present invention relates to a method for quantitative determination of a component in a sample by utilizing a reaction system which forms NAD(P)H, wherein NAD(P)H present in the sample or derived from components other than the objective component by reactions is eliminated prior to the quantitative determination of the objective component by utilizing the system which forms NAD(P)H.

BACKGROUND ART

Several methods for determining a component in a sample by utilizing oxidoreductase which catalyzes a reaction involving NAD(P)-NAD(P)H are known.

The methods are advantageous in stoichiometrical accuracy, small influence of other components, and the like. However, when NAD(P)H derived from components other than the objective component (hereinafter referred to as other components) is added during the determination, such NAD(P)H must be avoided or removed.

To avoid or remove such NAD(P)H, there is a method in which a reagent blank test is separately carried out and after determination of other components (so called blank test of a sample), the sum of NAD(P)H derived from the other components and the objective components is determined and the amount of the objective component is determined by calculation.

For example, in the case of determination of amylase activity in blood, the enzyme reaction described below is carried out and the rate of formation of NAD(P)H is determined, whereby the amylase activity can be determined. However, as maltose and glucose are contained in blood, NAD(P)H must be determined after they are removed or decomposed.

(1) maltopentose →(amylase)→ maltose + maltotriose

(2) maltose + Pi →(maltose phosphorylase)→ glucose-1-P + glucose

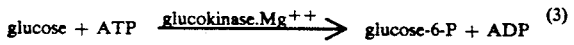

(3) glucose + ATP →(glucokinase·Mg++)→ glucose-6-P + ADP

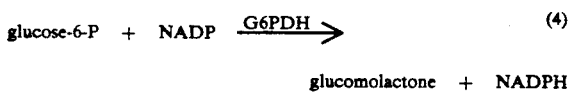

(4) glucose-6-P + NADP →(G6PDH)→ glucomolactone + NADPH

In the quantitative determination of NAD(P)H by colorimetry of the reaction solution, the absorbancy of the objective component is added to those of the other components, and the determinable range becomes narrow, depending upon the amount of glucose or maltose in a sample. The reason is that the absorbancy which is detectable with a spectrophotometer according to the currently employed technique is limited to a certain range; that is, it is impossible to detect an absorbancy of 3.0 ABS or more with an ordinary spectrophotometer. In view of this aspect, a region in which a measurement value is low is preferred. Further, in the case of reagent blank test with a high absorbancy, reproducibility is poor. Assuming that blank solutions have absorbancies of, for example, A and B (A<<B) respectively, the absorbancy E(E<<B) appearing as the result of reaction is added to form A+E and B+E (A+E<<B+E). When this run is repeated with measurements, the respective variations referred to as As and Bs are obtained (variations in the blank are similarly referred to as Ab and Bb, respectively). From the nature of a spectrophotometer as an apparatus, the percent transmission (T %) is logarithmically converted to absorbancy. Thus, a difference based on the logarithmic function appears on the variation in absorbancy in the case of low absorbancy (high percent transmission) and on the variation in absorbancy in the case of high absorbancy (low percent transmission), and even though the variations in percent transmission are identical, As<Bs (Ab<Bb) (absorbancy=log $I_0/I$, wherein I is transmittance). From the foregoing, the difference E is calculated for each of the blanks A and B.

With respect to A:

$$(A+E) \pm As - A \pm Ab = E \pm As \pm Ab$$

With respect to B:

$$(B+E) \pm Bs - B \pm Bb = E \pm Bs \pm Bb$$

From As<Bs and Ab<Bb is led, As+Ab<Bs+Bb; that is, when the blank has a large value, the variation becomes large, so that the coefficient of variation obtained by division by E becomes large.

An object of the present invention is to provide a method for quantitative determination of the objective component utilizing an NAD(P)H-forming reaction system without performing a blank test of the sample, by eliminating NAD(P)H formed from the other components or present in the sample by reactions.

DISCLOSURE OF THE INVENTION

According to the present invention, the objective component in a sample can be quantitatively determined by converting NAD(P)H present in the sample or formed from components other than the objective component into NAD(P) by the action of glutathione reductase (referred to as GR) in the presence of glutathione of oxidation type [hereinafter referred to as G(OX)] (first reaction); decomposing G(OX) by the action of γ-glutamyl transpeptidase (hereinafter referred to as γ-GTP) in the presence of glycine, glycylglycine or an equivalent thereof, or decomposing G(OX) to glutathione of reduction type [hereinafter referred to as G(OH)] with a mercapto compound and at the same time decomposing G(OX) and G(OH) with γ-GTP (second reaction); and then quantitatively determining the objective component utilizing the reaction system forming NAD(P)H. The objective component includes both of a substrate and an activity of an enzyme which participate in a reaction led to the NAD(P)H-forming reaction system.

Figure 1:
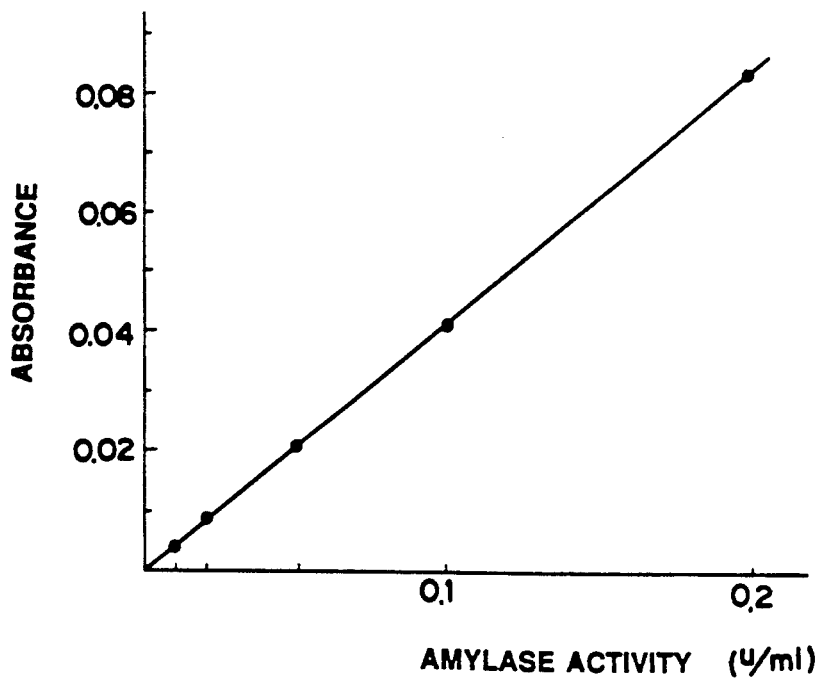
FIG. 1 shows the change in absorption of the reaction solution at 340 nm determined in accordance with the method of the present invention.

The present invention is described in detail below.

In the first reaction, G(OX) and glutathione reductase are added to a sample, if necessary, together with a substrate or an enzyme necessary for the reaction for forming NAD(P)H from the other components during the course of forming NAD(P)H from the objective component. The mixture is subjected to reaction in an appropriate buffer solution to convert NAD(P)H present in the sample or formed from the other components into NAD(P). G(OX) is used in an amount equivalent to that of NAD(P)H to be eliminated or more, preferably more than 1.5 times the amount of NAD(P)H. Glutathione reductase and the buffer solution are used in concentrations of 0.1 to 20 U/ml and 0.001 to 2M, respectively. The reaction is carried out at a temperature of 25° to 50° C. at pH 6 to 9 and is completed in several minutes.

Examples of the buffer are 3-(N-morpholino)propanesulfonic acid (MOPS), N-tris(hydroxymethyl)-methyl-2-aminoethanesulfonic acid (TES), Tris-hydrochloride, phosphate, borate, oxalate and Good's buffers.

In the second reaction, G(OX) present in the reaction solution after the first reaction is decomposed by γ-GTP. The decomposition of G(OX) can be accelerated by allowing the mercapto compound to exist. The mercapto compound converts G(OX) into G(OH) and G(OH) is readily decomposed by γ-GTP. The decomposition of G(OX) and G(OH) by γ-GTP is carried out in the presence of glycine, glycylglycine or an equivalent thereof. Examples of the reactions are shown by the reaction formulae (6) and (7) below. The equivalent mentioned above refers to a compound that can react with G(OX) and G(OH) by the action of γ-GTP and thereby can be converted into a substance which does not affect the subsequent quantitative determination of NAD(P)H. Glycylglycine, etc. are used in an amount equivalent to that of G(OX) or more, usually in an amount of 3 to 10 equivalents based on G(OX). The reaction is carried out at a temperature of 25° to 50° C. at pH 6 to 9. The mercapto compound is added in an amount equivalent to that of G(OX) or more, preferably in an amount of more than 1.5 equivalents based on G(OX). γ-GTP is used in an amount of 0.1 to 500 U/ml. As the mercapto compound, any compound having SH group and which does not inhibit the enzyme used is usable. Examples of the mercapto compound include dithiothreitol (DTT), 2-mercaptoethanol, cysteine or salts thereof, N-acetylcysteine or salts thereof, homocysteine or salts thereof, cysteamine or salts thereof, 2-mercaptoethanesulfonate, 3-mercapto-1,2-propanediol, 2-mercaptopropionate, 3-mercaptopropionate, mercaptosuccinate, thiomalate, 1-thioglycerine and dithioerythritol.

In cases where the formed NAD(P)H is quantitatively determined by measuring the absorption at 340 nm, it is preferred to use the mercapto compound having no absorption at 340 nm.

As the third reaction, when the objective component is a substrate, the substrate is decomposed to lead to the NAD(P)H-forming reaction and the formed NAD(P)H is quantitatively determined in a conventional manner.

When the objective component is an enzyme, a substrate for the enzyme is added and, if necessary, other enzymes are further added to lead to the NAD(P)H-forming reaction, and the rate of formation of NAD(P)H is determined.

Any known methods and methods which will be developed in the future are applicable to the quantitative determination of NAD(P)H formed by the reaction, unless they are unsuitable for the object of the present invention.

There are known, for example, a method in which the absorption is measured at 340 nm (UV method); the fluorescence method in which the absorption is measured at 365 nm or 460 nm; a method which comprises subjecting NAD(P)H to reaction with diaphorase or phenazine methosulfate, and tetrazolium salt, and measuring the absorption in a visible region; a method which comprises subjecting NAD(P)H to reaction with a chromogen in the presence of peroxidase or thiol oxidoreductase, and diaphorase, and quantitatively determining the dye formed; and a method which comprises converting NAD(P)H into a signal of hydrogen peroxide and quantitatively determining the signal (Japanese Published Unexamined Patent Applications Nos. 43398/85, 180600/85, 205999/84, 106299/84 and 32867/84).

In cases where the sample is a vital component or the like, a variety of surface active agents (for example, nonionic, anionic and cationic surface active agents such as polyoxyethylene higher aliphatic ethers or esters thereof, polyoxyethylene sorbitan higher fatty acid esters, polyoxyethylene-polyoxypropylene copolymer, polyoxyethylene higher aliphatic phenyl ethers, higher fatty acid sodium salts and sodium higher aliphatic benzenesulfonates) and lipases (for example, lipoprotein lipase) are used as lipid-solubilizing agents, etc. In addition, chelating agents (for example, EDTA or salts thereof, GEDTA, CYDTA, TTHA and IDA) and enzyme activators (for example, magnesium salts, calcium salts and zinc salts) are appropriately used. Furthermore, if necessary, specific enzyme inhibitors, for example, amylase inhibitor (made from wheat), lipase inhibitor, enzyme inhibitory antibody (monoclonal or polyclonal), and glutathione derivatives which are inhibitors of glutathione reductase may be used in order to terminate the enzyme reaction.

In the case of the aforesaid amylase determination, which is taken as an example of the determination of a component that achieves excellent results by the method of the present invention, addition of NAD(P), ATP, glucokinase (or hexokinase), G6PDH, maltose phosphorylase, glutathione reductase, G(OX) and phosphate to a sample results in formation of NAD(P)H derived from glucose and maltose in the sample and the formed NAD(P)H is converted into NAD(P).

The reactions described above are represented by the reaction formulae (1) through (4) given hereinabove and additionally the following formula:

(5)

Then, by addition of maltopentose which is a substrate for amylase, OTT, γ-GTP and glycylglycine, the remaining G(OX) is converted into G(OH) by the reducing power of DTT and at the same time, G(OX) is converted into glutamylglycylglycine and cystine by γ-GTP and G(OH) is converted into glutamylglycylglycine and cysteinylglycine.

(6)

Glutamylglycylglycine + cystinglbis(glycine)

$$G(OH) + \text{glycylglycine} \xrightarrow{\gamma\text{-GTP}} \text{glutamylglycylglycine} + \text{cysteinylglycine} \quad (7)$$

The added maltopentose is decomposed by amylase and NAD(P)H is formed according to the reaction formulae (1) through (4) shown above. By measuring the absorbancy of the reaction solution at 340 nm, NAD(P)H can be quantitatively determined and accordingly, amylase can be quantitatively determined.

Other examples of the determination of components which achieves excellent results by applying the present invention are shown below.

(1) Quantitative determination of amylase (A) (elimination of maltose and glucose which are originally present)

Maltose which is originally present is decomposed by maltose phosphorylase (MP) in the presence of phosphate. The formed glucose and glucose which is originally present are decomposed by glucose dehydrogenase in the presence of NAD(P), and then the formed NAD(P)H is eliminated. After G(OX) is decomposed, maltopentose is added and decomposed by amylase in the sample. The formed maltose is quantitatively determined.

(2) Quantitative determination of amylase (B) (elimination of maltose which is originally present)

Maltose which is originally present is decomposed in the same manner as in (1). The formed glucose-1-P is converted into glucose-6-P by phosphoglucomutase. Glucose-6-P is acted on by glucose-6-P-dehydrogenase (G6PDH), and the formed NAD(P)H is eliminated. After G(OX) is decomposed, maltopentose is added and the amylase activity is measured.

(3) Quantitative determination of maltose (elimination of glucose which is originally present)

Glucose which is originally present is decomposed by glucose dehydrogenase in the presence of NAD(P), and the formed NAD(P)H is eliminated. After G(OX) is decomposed, MP is added and maltose is quantitatively determined.

(4) Lipase activity (elimination of free glycerol which is originally present)

Free glycerol which is originally present is decomposed by glycerol dehydrogenase (G.DH), and the formed NADH is eliminated. After G(OX) is decomposed, glycerol ester is added and the formed glycerol is quantitatively determined, whereby the lipase activity is determined.

(5) Quantitative determination of glycerol ester (elimination of free glycerol which is originally present)

Free glycerol is decomposed by G.DH, followed by elimination of the formed NADH. After G(OX) is decomposed, lipase is added and the formed glycerol is quantitatively determined, whereby glycerol ester is determined.

(6) Choline esterase activity (elimination of free choline which is originally present)

Free choline is decomposed by choline dehydrogenase and betaine aldehyde dehydrogenase, and the formed NADH is eliminated. After G(OX) is decomposed, choline ester is added and the rate of formation of choline is measured, whereby the choline esterase activity is determined.

(7) Lipase activity (elimination of free fatty acids which are originally present)

Free fatty acids are converted into acyl CoA by CoA and acyl CoA synthetase. The acyl CoA is decomposed by 2-enoylacyl-CoA hydrolyase, L-3-hydroxyacyl-CoA, NAD oxidoreductase, acyl-CoA: acetyl CoA.C-acetyltransferase complex enzyme (HDT) and acyl CoA oxidase, followed by elimination of the formed NADH. After G(OX) is decomposed, glycerol ester is added and the formed fatty acids are quantitatively determined, whereby the lipase activity is determined.

As illustrated above, in cases where the component ($\alpha$) formed during the course of leading the objective component into the NAD(P)H-forming reaction is originally contained in a sample, the objective component in the sample can be determined accurately by leading the component ($\alpha$) originally contained in the sample into the NAD(P)H-forming reaction; eliminating the formed NAD(P)H by the method of the present invention; leading the objective component into the NAD(P)H-forming reaction system; and then determining the formed NAD(P)H.

Certain embodiments of the present invnetion are illustrated by the following examples.

EXAMPLE 1 (DETERMINATION OF AMYLASE ACTIVITY)

Reagent A

| | |
|---|---|
| MOPS buffer solution (Dojin Chemical Research Institute) pH: 7.5 | 0.1 M |
| Dipotassium phosphate | 10 mM |
| ATP | 2.5 mg/ml |
| Magnesium chloride | 2 mg/ml |
| Triton X-100 | 2 mg/ml |
| EDTA | 0.1 mg/ml |
| Maltose phosphorylase | 10 U/ml |
| Glucokinase | 5 U/ml |
| NADP | 1 mg/ml |
| GP6DH | 5 U/ml |
| GR | 3 U/ml |
| G(OX) | 0.5 mg/ml |

Reagent B

| | |
|---|---|
| MOPS (pH: 7.5) | 0.1 M |
| Maltopentose | 4 mg/ml |
| DTT | 5 mg/ml |
| $\gamma$-GTP | 10 U/ml |
| Glycylglycine | 5 mg/ml |

Reagent C

The same composition as that of Reagent A except that GR and G(OX) are not contained.

Reagent D

The same composition as that of Reagent B except that DTT is not contained.

When Reagents A and B are used, NADPH derived from glucose and maltose in a sample is eliminated, followed by measurement of the amylase activity, in which maltopentose acts as a substrate.

When Reagents C and D are used instead of Reagents A and B, NADPH derived from glucose and maltose is not eliminated but remains.

Test 1.

Reagent A (1.5 ml) was placed in a cell for a spectrophotometer and heated at 37° C. for 5 minutes. Then, 0.02 ml each of samples respectively containing the substances shown in the table was added to the cell, followed by heating for further 5 minutes. Separately, 1.5 ml of Reagent B was heated at 37° C. and added to the mixture. Absorption of the reaction solution at 340 nm was traced.

Test 2.

In the procedure of Test 1, Reagents C and D were used instead of Reagents A and B, respectively. The test results show the absorption values of the reaction solutions.

| Sample No. | | Test 1 (ABS/min) | Test 2 |
|---|---|---|---|
| 1 | Glucose 10 mg/ml | constant at 0 | constant at 2.2 |
| 2 | Maltose 10 mg/ml | constant at 0 | constant at 1.17 |
| 3 | Amylase 100 mu/ml | increased with time, 0.0041 | same as in Test 1 |
| 4 | Glucose 10 mg/ml Amylase 100 mu/ml | increased with time, 0.0041 | increased with time from 2.3 |
| 5 | Maltose 10 mg/ml Amylase 100 mu/ml | increased with time, 0.0041 | increased with time from 1.15 |
| 6 | Serum (containing 6.24 mg/ml glucose) | increased with time, 0.0025 | increased with time from 1.5 |

The absorption values of Sample Nos. 1 and 2 in Test 2 result from glucose and maltose.

In Sample No. 3, neither glucose nor maltose is originally present and so NADPH to be eliminated is not formed.

In the case of Sample Nos. 4 and 5, after elimination of glucose or maltose which is originally present, maltopentose is decomposed by amylase in the samples and the absorption due to the formation of NADPH increases in Test 1. In Test 2, NADPH derived from glucose and maltose is included from the beginning. The results similar to those with Sample Nos. 4 and 5 are obtained with Sample No. 6.

The procedures of Test 1 and Test 2 were carried out using Sample No. 3 with a variety of the amylase activity, i.e. 10 mu/m±, 20 mu/ml, 50 mu/ml, 100 mu/ml and 200 mu/ml. Reagent B or D was added thereto and the absorbancy was measured after 10 minutes to prepare calibration curves.

Figure 2:
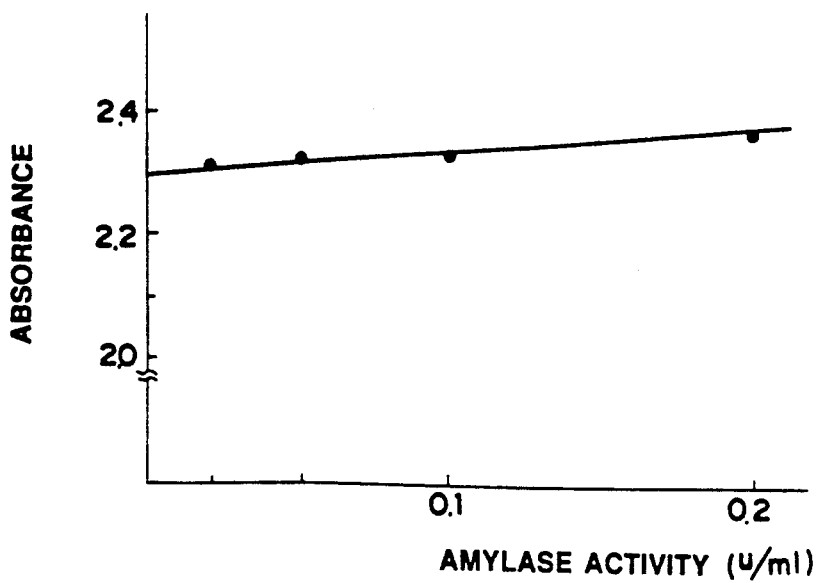
FIG. 2 shows the change in absorption in the case where NAD(P)H derived from the other components is added.

The calibration curves are shown in FIG. 1 (Test 1) and FIG. 2 (Test 2).

With respect to the test using Sample No. 6, the absorption was measured 5 minutes after the addition of Reagent B or D (initiation of the absorption due to the amylase reaction) and 10 minutes after the addition and the mean rate of change (ΔE) was calculated to determine the amylase activity. Test 1 and Test 2 were repeated 10 times, respectively, and the coefficients of variation (CV %) obtained are shown in the table below.

TABLE 1

| Number | Test 1 (U/l) | Test 2 (U/l) |
|---|---|---|
| 1 | 58.6 | 71.8 |
| 2 | 60.7 | 48.7 |
| 3 | 62.5 | 73.7 |
| 4 | 59.8 | 62.6 |
| 5 | 61.6 | 48.2 |
| 6 | 61.8 | 59.4 |
| 7 | 64.0 | 61.6 |
| 8 | 59.5 | 71.2 |
| 9 | 62.5 | 62.5 |
| 10 | 61.4 | 51.7 |
| Mean Value | 61.2 | 61.1 |
| CV (%) | 2.5% | 14.5% |

As is clear from the table, Test 1 provides results much superior to those of Test 2 in reproducibility.

EXAMPLE 2

The same experiment as in test 1 of Example 1 was carried out using Sample No. 6, except that 12 U/ml glucose dehydrogenase was used instead of ATP, glucokinase, and G6PDH. The results are shown below.

TABLE 2

| Number | Amylase value (mu/ml) |
|---|---|
| 1 | 59.2 |
| 2 | 61.9 |
| 3 | 62.1 |
| 4 | 61.4 |
| 5 | 60.2 |
| 6 | 61.5 |
| 7 | 62.3 |
| 8 | 60.0 |
| 9 | 61.0 |
| 10 | 63.1 |
| Mean | 61.3 mu/ml |
| CV = 1.84% | |

EXAMPLE 3

The same experiment as in Test 1 of Example 1 was carried out using Sample No. 6 supplemented with 20 mg/ml maltose, except that 0.1 mg/ml glucose-1,6-diphosphate and 5 U/ml phosphoglucomutase were used instead of ATP and glucokinase. The results are shown in Table 3.

TABLE 3

| Number | Amylase value (mu/ml) |
|---|---|
| 1 | 60.4 |
| 2 | 59.3 |
| 3 | 60.6 |
| 4 | 59.5 |
| 5 | 63.2 |
| 6 | 58.0 |
| 7 | 60.1 |
| 8 | 63.1 |
| 9 | 60.8 |
| 10 | 63.0 |
| Mean | 60.8 mu/ml |
| CV = 2.77% | |

EXAMPLE 4

The same experiment as in Test 1 of Example 1 was carried out using Sample No. 6, except that 5 U/ml hexokinase was used instead of glucokinase. The results are shown in Table 4.

TABLE 4

| Number | Amylase value (mu/ml) |
|---|---|
| 1 | 60.8 |
| 2 | 60.7 |
| 3 | 61.7 |
| 4 | 61.0 |
| 5 | 60.6 |
| 6 | 61.2 |
| 7 | 61.3 |
| 8 | 61.4 |
| 9 | 61.4 |
| 10 | 61.2 |
| Mean | 61.2 mu/ml |
| CV = 0.51% | |

EXAMPLE 5

Reagent A

| | |
|---|---|
| TES buffer solution (pH 6.75) | 0.04 M |
| Pluronic F-68 | 1 mg/ml |
| 1,2-Dilinolein | 1.33 mM |
| Co-A | 2 mM |
| Co-lipase | 0.1 mg/ml |
| $CaCl_2$ | 1.17 mM |
| NAD | 8.17 mM |
| ATP | 1 mM |
| Acyl CoA synthetase (ACS) | 1.7 U/ml |
| Acyl CoA oxidase (ACO) | 20 U/ml |
| HDT | 45 U/ml |
| $MgCl_2$ | 1.17 mM |
| GR | 5 U/ml |
| G(OX) | 0.8 mg/ml |

Reagent B

| | |
|---|---|
| TES buffer solution (pH 6.75) | 0.04 M |
| Pluronic F-68 | 1 mg/ml |
| Deoxycholic acid | 16.5 mM |
| Dithioerythritol | 5 mg/ml |
| γ-GTP | 10 U/ml |
| Glycylglycine | 8 mg/ml |

Serum (0.02 ml) having the lipase content of 55.4 mu/ml as measured with the lipase assay kit lipase UV (Toyo Jozo Co., Ltd.) was added to 1.5 ml of Reagent A. After reaction at 37° C. for 3 minutes, Reagent B was added to the reaction mixture. Two minutes after the addition, the rate of increase in absorption of the reaction solution at 340 nm was measured to determine the lipase activity. The mean value of 10 measurements was 56 U/ml with CV of 1.8%.

EXAMPLE 6

The same procedure as in Example 5 was carried out, except that 1-monolinolein was used instead of 1,2-dilinolein and glycerol dehydrogenase was used instead of ACS, ACO, HDT and CoA. Test 1 gave the result of 55.1 U/l with CV of 2.7%.

We claim:

1. In a method for determination of amylase activity in a biological sample, which comprises the steps of:
   (1) mixing the sample with NAD(P), ATP, glucokinase, glucose-6-P-dehydrogenase, maltose phosphorylase and phosphate to form a first reaction solution;
   (2) subjecting the first reaction solution to reaction with maltopentose to form a second reaction solution; and
   (3) measuring the absorption of the second reaction solution at 340 nm, the improvement comprising: carrying out the reaction of step (1) at 25° to 50° C. at pH 6 to 9 in the presence of glutathione reductase and glutathione of oxidation type; and carrying out the reaction of step (2) at 25° to 50° C. at pH 6 to 9 in the presence of dithiothreitol, γ-glutamyl transpeptidase and glycylglycine.

2. In a method for determination of amylase activity in a biological sample, which comprises the steps of:
   (1) mixing the sample with NAD(P), phosphate, maltose phosphorylase, β-phosphoglucomutase, glucose-6-P-dehydrogenase and at least one of glucose-1,6-diphosphate or fructose-1,6-diphosphate to form a first reaction solution;
   (2) subjecting the first reaction solution to reaction with maltopentose to form a second reaction solution; and
   (3) measuring the absorption of the second reaction solution at 340 nm, the improvement comprising: carrying out the reaction of the step (1) at 25° to 50° C. at pH 6 to 9 in the presence of glutathione reductase and glutathione of oxidation type; and carrying out the reaction of step (2) at 25° to 50° C. at pH 6 to 9 in the presence of dithiothreitol, γ-glutamyl transpeptidase and glycylglycine.

3. In a method for quantitative determination of NAD(P)H formed by an enzymatic reaction in which an objective enzyme or substrate in a sample participates, the improvement comprising, prior to said quantitative determination, carrying out the steps of:
   (1) converting to NAD(P) the NAD(P)H present in a sample or formed by an enzymatic reaction in which the objective enzyme or substrate does not participate using glutathione reductase at 25° to 50° C. at pH 6 to 9 and glutathione of oxidation type; and
   (2) decomposing the remaining glutathione of oxidation type using γ-glutamyl transpeptidase at 25° to 50° C. at pH 6 to 9 and glycine or glycylglycine, in the optional presence of a mercapto compound.

4. A method according to claim 3, wherein said quantitative determination of NAD(P)H is effected by measuring the ultraviolet absorption of a solution containing NAD(P)H at 340 nm.

5. A method according to claim 3, wherein said objective enzyme or substrate in a sample is a member selected from the group consisting of amylase, maltose, lipase, glycerol ester and choline esterase.

6. A method according to claim 3, wherein said mercapto compound is a member selected from the group consisting of dithiothreitol (DTT), 2-mercaptoethanol, cysteine or salts thereof, N-acetylcysteine or salts thereof, homocysteine or salts thereof, cysteamine or salts thereof, 2-mercapto-ethanesulfonate, 3-mercapto-1,2-propanediol, 2-mercaptopropionate, 3-mercaptopropionate, mercaptosuccinate, thiomalate, 1-thioglycerine and dithioerythritol.

7. A method for quantitatively determining NAD(P)H comprising the steps of:
   (a) oxidizing a sample using oxidized glutathione and glutathione reductase;
   (b) decomposing the oxidized glutathione remaining in the sample using γ-glutamyl transpeptidase at 25° to 50° C. at pH 6 to 9 in the presence of glycine, glycylglycine or an equivalent thereof;
   (c) forming NAD(P)H in a reaction using a component present in the sample;
   (d) quantitatively determining any NAD(P)H formed in said reaction; and
   (e) correlating the amount of component present in the sample from the amount of NAD(P)H determined in step (d).

8. A method according to claim 7, wherein the NAD(P)H formed in step (c) is quantitated by measuring the ultraviolet absorption of the sample at 340 nm.

9. A method according to claim 7, wherein the component of step (c) is selected from the group consisting of amylase, maltose, lipase, glycerol ester and choline esterase.

10. A method according to claim 7, wherein the decomposing step is conducted in the presence of a mercapto compound selected from the group consisting of dithiothreitol, 2-mercaptoethanol, cysteine or salts thereof, N-acetylcysteine or salts thereof, homocysteine or salts thereof, cysteamine or salts thereof, 2-mercaptoethanesulfonate, 3-mercapto-1,2-propandiol, 2-mercaptopropionate, 3-mercaptopropionate, mercaptosuccinate, thiomalate, 1-thioglycerine and dithioerythritol.

* * * * *